(12) United States Patent
Fujimori et al.

(10) Patent No.: US 8,974,836 B2
(45) Date of Patent: Mar. 10, 2015

(54) ANGIOGENESIS REGULATING COMPOSITION AND METHOD FOR REGULATING ANGIOGENESIS

(71) Applicants: Junya Fujimori, Matsumoto (JP); Hidekazu Baba, Matsumoto (JP); Toshinori Murata, Matsumoto (JP)

(72) Inventors: Junya Fujimori, Matsumoto (JP); Hidekazu Baba, Matsumoto (JP); Toshinori Murata, Matsumoto (JP)

(73) Assignee: Air Water, Inc., Hokkaido (JP)

(*) Notice: Subject to any disclaimer, the term of this patent is extended or adjusted under 35 U.S.C. 154(b) by 0 days.

(21) Appl. No.: 13/897,603

(22) Filed: May 20, 2013

(65) Prior Publication Data

US 2013/0251823 A1    Sep. 26, 2013

Related U.S. Application Data

(62) Division of application No. 13/383,805, filed as application No. PCT/JP2010/061768 on Jul. 12, 2010.

(30) Foreign Application Priority Data

Jul. 17, 2009  (JP) ................................. 2009-168928
Jun. 3, 2010   (JP) ................................. 2010-128057

(51) Int. Cl.
 A61K 33/00    (2006.01)
 A61K 31/21    (2006.01)
 A61K 33/26    (2006.01)

(52) U.S. Cl.
 CPC ................. *A61K 33/00* (2013.01); *A61K 31/21* (2013.01); *A61K 33/26* (2013.01)
 USPC ...................................................... 424/718

(58) Field of Classification Search
 None
 See application file for complete search history.

(56) References Cited

U.S. PATENT DOCUMENTS

| 6,150,407 A * | 11/2000 | Tuse et al. ...................... 514/532 |
| 2007/0135380 A1 * | 6/2007 | Bednarski et al. ............... 514/64 |
| 2008/0069904 A1 * | 3/2008 | Oronsky et al. ................ 424/702 |
| 2010/0197702 A1 | 8/2010 | Hellberg et al. |
| 2011/0144073 A1 * | 6/2011 | Benedini et al. ............... 514/174 |

FOREIGN PATENT DOCUMENTS

| JP | 09-508892 | 9/1997 |
| JP | 10-273450 | 10/1998 |
| JP | 2002-284685 | 10/2002 |
| JP | 2002-537810 | 11/2002 |
| JP | 2003-506394 | 2/2003 |
| JP | 2008-110950 | 5/2008 |
| JP | 2008-280356 | 11/2008 |
| WO | WO-95/13830 | 5/1995 |
| WO | WO-98/43621 A1 | 10/1998 |
| WO | WO-00/52160 | 9/2000 |
| WO | WO-01/10406 A2 | 2/2001 |
| WO | WO 2008/105731 | * 9/2008 | ............. A61K 33/00 |
| WO | WO-2008/105731 A1 | 9/2008 |

OTHER PUBLICATIONS

Zurakowski et al. "Nitrate therapy may retard glaucomatous optic neuropathy, perhaps through modulation of glutamate receptors". Vision Research vol. 38, Issue 10, May 1998, pp. 1489-1494.*

"Arteriosclerosis, Thrombosis, and Vascular Biology Annual Conference 2009", Arteriosclerosis, Thrombosis, & Vascular Biology, vol. 29, No. 7, Jun. 17, 2009, pp. e9-e130, XP055044137, ISSN: 1079-5642 DOI: 10.1161/ATV.0B013E3181AB66E7, *Abstract No. P255; p. e58.

Banin, E. et al. "T2-TrpRS Inhibits Preretinal Neovascularization and Enhaces Physiological Vascular Regrowth in OIR as Assessed by a New method of Quantification", Investigative Ophthalmology & Visual Science, May 2006, Vo. 47, No. 5, pp. 2125-2134.

Dimmeler, S. et al. "Upregulation of Superoxide Dismutase and Nitric Oxide Synthase Mediates the Apoptosis-Suppressive Effects of Shear stress on endothelial Cells", Arterioscler Thromb Vasc Biol, 1999, vol. 19, pp. 656-664.

Huang, Z. et al. "Enzymatic function of hemoglobin as a nitrite reductase that produces NO under allosteric control", The Journal of Clinical Investigation, Aug. 2005, vol. 115, No. 8, pp. 2099-2107.

International Search Report in PCT/JP2010/061768 dated Aug. 10, 2010.

Kumar, D. et al. "chronic sodium nitrite therapy augments ischemia-induced angiogenesis and arteriogenesis" Proceedings of the National Academy of Sciences of the United States of America, 2008, vol. 105, No. 21, pp. 7540-7545.

(Continued)

*Primary Examiner* — Robert A Wax
*Assistant Examiner* — Danah Al-Awadi
(74) *Attorney, Agent, or Firm* — Foley & Lardner LLP

(57) ABSTRACT

An angiogenesis regulating composition used to treat/prevent an angiogenic disease in a subject, that contains in an effective amount at least one of nitrate, nitrite, and a compound convertible into nitrate or nitrite after the compound is absorbed into the subject, and an angiogenesis regulation method administering to a subject a composition containing as an active ingredient at least one of nitrate, nitrite, and a compound convertible into nitrate or nitrite after the compound is absorbed into the subject, provide a composition effective in treating and preventing angiogenic diseases, that can medically control angiogenic diseases, and medically regulate angiogenesis in ophthalmologic diseases in particular, and allows treatment without inhibiting physiological neovascularization, with a limited side effect and significantly safely, and an angiogenesis regulation method using the same.

5 Claims, 4 Drawing Sheets

(56) References Cited

OTHER PUBLICATIONS

Mazzone, M. et al. "Drug discovery: a Lifeline for suffocating tisses", Nature, 2008, vol. 453, No. 7199, pp. 1194-1195.
Murohara, T. et al. "Nitric Oxide and Angiogenesis in Cardiovascular Disease", Antioxidants & Redox Signaling, Nov. 5, 2002, vol. 4, No. 5, pp. 825-831.
Noiri, E. et al. "Podokinesis in endothelial cell migration: role of nitric oxide", The American Physiological Society, 1998, vol. 274, pp. 236-244.
Non-Final Office Action in U.S. Appl. No. 13/383,805 dated Jan. 31, 2013.
Non-Final Office Action U.S. Appl. No. 13/383,805 dated Mar. 19, 2013.
Smith, L. et al. "Oxygen-Induced Retinopathy in the Mouse", Investigative Ophthalmology Visual Science, 1994, vol. 35, pp. 101-111.
Supplementary European Search Report EP 10 79 9813 dated Nov. 21, 2012.
Yoshida, K. et al. "Metabolic Fate of Nitric Oxide", Intl Archives of Ocupational and Environmental Health, 1980, vol. 46, pp. 71-77.
Ziche, M. et al. "Nitric Oxide Promotes Proliferation and Plasminogen Activator production by Coronary Venular Endothelium Through Endogenous bFGF", Circulation Research, 1997, vol. 80, pp. 845-852.
Office Action received in corresponding U.S. Appl. No. 13/383,805 dated Mar. 13, 2014.

\* cited by examiner (a)

(b)

(c)

(d)

(a)

(b)

(c)

(a)

(b)

(c)

(a)

(b)

ANGIOGENESIS REGULATING COMPOSITION AND METHOD FOR REGULATING ANGIOGENESIS

TECHNICAL FIELD

The present invention relates to a composition used to regulate angiogenesis to treat and prevent angiogenic diseases, and a method for regulating angiogenesis.

BACKGROUND ART

Angiogenesis refers to formation of a new blood vessel branch by endothelial cell proliferation and migration and remodeling from a pre-existing blood vessel of a tissue. In recent years, the mechanism of angiogenesis has drastically been revealed by cell biological approaches. Angiogenesis is started by induced expression of VEGF (vascular endothelial growth factor) mRNA which occurs by activation of a transcription factor HIF (hypoxia-inducible factor) responding to ischemia-based hypoxia. The produced VEGF binds to a VEGF receptor (VEGFR) localized in a vascular endothelial cell, and activates an intracellular signaling pathway. This results in decomposed extracellular basement membrane, followed stepwise by vascular endothelial cell migration/proliferation, lumen formation of vascular endothelial cell, basement membrane formation, and pericyte enclosure, finally resulting in angiogenesis.

According to Murohara T. et al., "Nitric Oxide and Angiogenesis in Cardiovascular Disease", Antioxidants & Redox Signaling, Vol. 4, pp. 825-831 (2002) (NPL 1), a pathway starting from phosphatidylinositol-3-kinase (PI3K) is clarified as an intracellular signaling pathway involved in angiogenesis. In the PI3K pathway, activation of endothelial NO synthase (eNOS), and thereby increasing NO production, are confirmed, and according to Noiri E. et al., "Podokinesis in endothelial cell migration: role of nitric oxide", The American Physiological Society, Vol. 274, pp. 236-244 (1998) (NPL 2), Ziche M. et al., "Nitric Oxide Promotes Proliferation and Plasminogen Activator Production by Coronary Venular Endothelium Through Endogenous bFGF", Circulation Research, Vol. 80, pp. 845-852 (1997) (NPL 3), and Dimmeler S. et al., "Upregulation of Superoxide Dismutase and Nitric Oxide Synthase Mediates the Apoptosis-Suppressive Effects of Shear Stress on Endothelial Cells", Arterioscler. Thromb. Vasc. Biol., Vol. 19, pp. 656-664 (1999) (NPL 4), currently it is believed that endogenous nitrogen monoxide promotes angiogenesis by its vascular endothelial cell proliferation and migration promoting effect and an apoptosis-suppressive effect.

In clinical medicine, it is known that angiogenesis has a large influence on wound-healing and the progress of many diseases. Diseases known as involving angiogenesis include retinopathy of prematurity, diabetic retinopathy, age-related macular degeneration, neovascular glaucoma and other ophthalmologic diseases, rheumatoid arthritis and other inflammatory diseases, solid tumors and other malignant neoplasms, and the like, and these diseases present pathologic neovascularization lacking a regulation mechanism. For ophthalmologic diseases, pathologic neovascularization has been treated strategically consistently by its suppression and inhibition, generally categorized into surgical treatment and medication, as disclosed in Japanese Patent Laying-Open No. 2002-284685 (PTL 1) and Japanese Patent Laying-Open No. 2008-110950 (PTL 2).

Although a laser photocoagulation is generally used as a representative surgical treatment, this treatment is compensatory tissue destruction applied reluctantly in a pathologically advanced stage, which may cause reducing peripheral vision loss and night vision difficulties, and a change of color vision.

In medication, inhibitors which block different stages of an intracellular signaling pathway in angiogenesis have been studied and developed by molecular-biologically elucidating mechanism of angiogenesis. A VEGF antibody (Bevacizumab), and a nucleic acid (Pegaptanib sodium), which specifically binds to VEGF as described in Japanese Patent Laying-Open No. 2008-280356 (PTL 3), have been invented and developed as VEGF inhibitors. While these inhibitors are effective in inhibiting pathologic neovascularization of retinopathy and in diabetic macular edema, it has been reported that the anti-VEGF antibody inhibits physiological neovascularization and causes systemic wound-healing retardation, cerebral hemorrhage, cerebrovascular accidents, myocardial infarction, angina pectoris, and other serious side effects.

According to Eyal B. et al., "T2-TrpRS Inhibits Preretinal Neovascularization and Enhances Physiological Vascular Regrowth in OIR as Assessed by a New Method of Quantification", Investigative Ophthalmology & Visual Science, Vol. 47, pp. 2125-2134 (2006) (NPL 5), inhibition of pathologic neovascularization is attempted by suppressing production of endogenous nitrogen monoxide using a nitrogen monoxide synthase inhibitor. It is predicted that aggravation of diabetes as an underlying disease for retinopathy, elevation of blood pressure, myocardial infarction, angina pectoris and expression of other various systemic side effects are caused by strongly inhibiting molecules, such as nitrogen monoxide, that play a physiologically important role.

Furthermore, because VEGF inhibitor and other similar ophthalmovascular therapeutic agents are administered to a patient through intravitreous injection to alleviate a systemic side effect, this treatment imposes a large burden on the patients, and the intravitreous injection not only injures the patients' ocular tissues but will also constantly expose their lenses and retinal tissues to a risk of bacterial infection.

CITATION LIST

Patent Literature

PTL 1: Japanese Patent Laying-Open No. 2002-284685
PTL 2: Japanese Patent Laying-Open No. 2008-110950
PTL 3: Japanese Patent Laying-Open No. 2008-280356

Non-Patent Literature

NPL 1: Murohara T. et al., "Nitric Oxide and Angiogenesis in Cardiovascular Disease", Antioxidants & Redox Signaling, Vol. 4, pp. 825-831 (2002)
NPL 2: Noiri E. et al., "Podokinesis in endothelial cell migration: role of nitric oxide", The American Physiological Society, Vol. 274, pp. 236-244 (1998)
NPL 3: Ziche M. et al., "Nitric Oxide Promotes Proliferation and Plasminogen Activator Production by Coronary Venular Endothelium Through Endogenous bFGF", Circulation Research, Vol. 80, pp. 845-852 (1997)
NPL 4: Dimmeler S. et al., "Upregulation of Superoxide Dismutase and Nitric Oxide Synthase Mediates the Apoptosis-Suppressive Effects of Shear Stress on Endothelial Cells", Arterioscler. Thromb. Vasc. Biol., Vol. 19, pp. 656-664 (1999)
NPL 5: Eyal B. et al., "T2-TrpRS Inhibits Preretinal Neovascularization and Enhances Physiological Vascular Regrowth in OIR as Assessed by a New Method of Quantification", Investigative Ophthalmology & Visual Science, Vol. 47, pp. 2125-2134 (2006)

NPL 6: Katsumi Y. et al., "Metabolic Fate of Nitric Oxide", Int ArchOccup Environ Health, Vol. 46, pp. 71-77 (1980)

NPL 7: Zhi H. et al., "Enzymatic function of hemoglobin as a nitrite reductase that produces NO under allosteric control", The Journal of Clinical Investigation, Vol. 115, pp. 2099-2107 (2005)

NPL 8: Lois E. H. Smith et al., "Oxygen-Induced Retinopathy in the Mouse", Investigative Ophthalmology Visual Science, Vol. 35, pp. 101-111 (1994)

SUMMARY OF INVENTION

Technical Problem

As previously described, ophthalmologic angiogenic diseases have conventionally been treated mainly by surgical treatment accompanied by compensatory tissue destruction, or intravitreous medication with a high risk of inhibited physiological neovascularization, a critical systemic side effect, and bacterial infection, and there has been no established satisfactory surgical or medical treatment methodology.

The present invention has been made to address the above issue, and it contemplates a composition effective in treating and preventing angiogenic diseases, that can medically control angiogenic diseases, and medically regulate angiogenesis in ophthalmologic diseases in particular, and allows treatment without inhibiting physiological neovascularization, with a limited side effect and significantly safely, and an angiogenesis regulation method using the same.

Solution to Problem

In order to address the above issue, the present inventors have studied diligently and as a result found that nitrate/nitrite administered in a pharmaceutically acceptable amount has an effect regulating a process of angiogenesis. In particular, the present inventors have revealed that nitrate/nitrite can regulate angiogenesis in ophthalmologic disease and suppress pathological neovascularization without inhibiting physiological neovascularization, found out that these compounds are useful as a therapeutic and preventive medicine for ophthalmologic diseases such as retinopathy of prematurity, diabetic retinopathy (proliferative diabetic retinopathy, in particular), age-related macular degeneration, and neovascular glaucoma, and thus completed the present invention. That is, the present invention is as follows:

The present invention provides an angiogenesis regulating composition used to treat/prevent an angiogenic disease in a subject, characterized by containing in an effective amount at least one of nitrate, nitrite, and a compound convertible into one of nitrate and nitrite after it is absorbed into the subject.

Preferably, the present composition regulates angiogenesis by maintaining nitrate ions in an effective concentration range in the subject.

Preferably, the present composition contains at least one of nitrate, nitrite, and the compound in an amount providing a plasma concentration of nitrate ions within a range of 8 μmol/L to 1000 μmol/L when the composition is administered to the subject.

Preferably, the angiogenic disease is at least one ophthalmologic disease selected from retinopathy of prematurity, diabetic retinopathy, age-related macular degeneration, and neovascular glaucoma.

Preferably, the present composition is a pharmaceutical composition or at least one selected from health food, functional food, food for specified health use, and dietary supplement.

The present invention also provides an angiogenesis regulation method administering to a subject a composition containing as an active ingredient at least one of nitrate, nitrite, and a compound convertible into one of nitrate and nitrite after it is absorbed into the subject.

Preferably, the present method regulates angiogenesis by maintaining nitrate ions in an effective concentration range in the subject.

Preferably, the present method provides a plasma concentration of nitrate ions in the subject within a range of 8 μmol/L to 1000 μmol/L.

Advantageous Effects of Invention

The present invention can thus provide a composition effective in treating and preventing angiogenic diseases, that can medically control angiogenic diseases, and medically regulate angiogenesis in ophthalmologic diseases in particular, and allows treatment without inhibiting physiological neovascularization, with a limited side effect and significantly safely, and an angiogenesis regulation method using the same.

BRIEF DESCRIPTION OF DRAWINGS

FIGS. 1(a), 1(b), 1(c) and 1(d) are indicated in the case of administration of 15 μmol/kg of sodium nitrite, 75 μmol/kg of sodium nitrite, 75 μmol/kg of sodium nitrate, and physiological saline, respectively.

FIGS. 4(a), 4(b), and 4(c) are indicated in the case of administration of 15 μmol/kg of sodium nitrate, 15 μmol/kg of sodium nitrite, and physiological saline, respectively.

FIGS. 5(a), 5(b), and 5(c) are indicated in the case of administration of sodium nitroprusside (SNP), nitroglycerin (NTG), and 15 μmol/kg of sodium nitrite, respectively.

FIGS. 6(a) and 6(b) are indicated in the case of administration of anti-VEGF antibody, and 15 μmol/kg of sodium nitrite, respectively.

DESCRIPTION OF EMBODIMENTS

Figure 1:
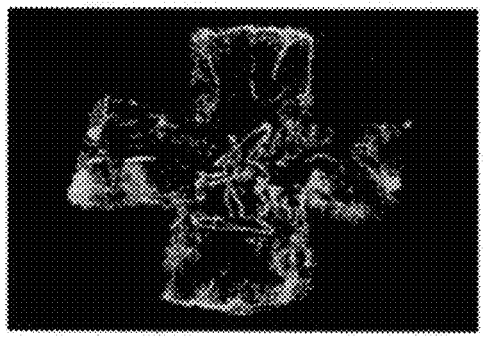
FIG. 1 shows a fluorescence imaging of retinal vessel obtained as a result of an exemplary experiment 1.
Figure 1:
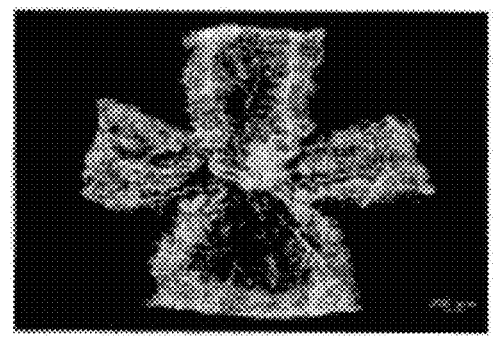
Figure 1:
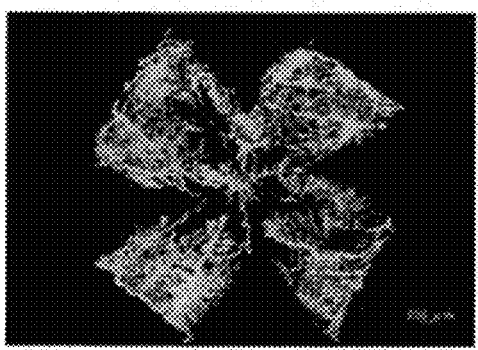
Figure 1:
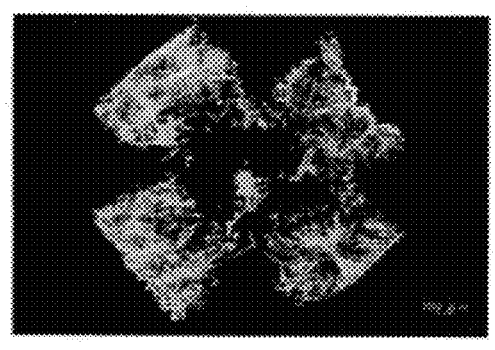

Originally, nitrate is widely distributed in the nature including soil, and is incorporated into human body mainly through intake of leaf vegetables. Nitrate is absorbed via a digestive tract satisfactorily and approximately 25% of nitrate having entered systemic circulation is secreted in saliva. A portion (approximately 30%) of nitrate in saliva is reduced to nitrite by dental bacteria and is re-absorbed via a digestive tract or is reduced to nitrogen monoxide by stomach acid and thus re-absorbed via a digestive tract. It has been reported that a healthy adult has a plasma concentration of nitrate ions of 10 μmol/L to 71 μmol/L and a plasma concentration of nitrite ions of 0.15 μmol/L to 1 μmol/L.

The present inventors have found that the plasma concentration of nitrate and nitrite ions is commonly low in premature babies, subjects undergoing a high-concentration of oxygen therapy, diabetics, hypertensives and the like, and that angiogenesis can be regulated by recovering these ion concentrations in plasma to a normal value or increasing them to a therapeutically effective concentration. That is, the present composition supplements nitrate ions and nitrite ions that should inherently be present in the body to maintain homeostasis of angiogenesis, and the present composition is thus also applicable to newborns significantly safely.

The present composition is a composition which regulates angiogenesis that is used to treat/prevent diseases of subjects that are accompanied by angiogenesis, and it is characterized by containing at least one of nitrate, nitrite, and a compound convertible into one of nitrate and nitrite after it is absorbed into the subject (hereinafter generally referred to as an "active ingredient") in an amount effective in treating/preventing angiogenic diseases.

In the present invention, nitrate/nitrite is only required to be a pharmaceutically acceptable salt formed of inorganic anions (nitrate ion: $NO_3^-$, nitrite ion: $NO_2^-$) and cations, and for example the cation can be of an alkaline metal, an alkaline earth metal, or an organic base. For example, preferable alkaline metals are sodium and potassium, preferable alkaline earth metals are calcium and magnesium, and preferable organic bases are arginine and lysine.

Furthermore, the present compound convertible into one of nitrate and nitrite after it is absorbed into a subject means a compound which is absorbed through oral/parenteral administration, rapidly metabolized, and circulates systemically in the form of nitrate or nitrite. Such a compound is exemplified by nitric oxide, such as nitrogen monoxide, as is also described in Katsumi Y. et al., "Metabolic Fate of Nitric Oxide", Int ArchOccup Environ Health, Vol. 46, pp. 71-77 (1980) (NPL 6).

Note that about the present composition, nitrate has not been reported to have particular serious side effect, however nitrite has been reported to cause methemoglobinemia as acute and subacute toxicity. However, the amount of nitrite administered to exhibit the effect of the present invention is approximately ⅛ or smaller of a maximal no-effect dose for methemoglobinemia reported for Rodentia (84 mg/kg/day for sodium nitrite) and thus also provides a safe treatment for newborns.

As has been mentioned above, endogenous nitrogen monoxide has an effect to promote proliferation and migration of vascular endothelial cells and plays an important role in angiogenesis, and it is believed that the angiogenesis regulation mechanism by nitrate and nitrite in the present invention involves a mechanism of conversion of nitrite ions to nitrogen monoxide that proceeds in a condition with tissue ischemia, such as described for example in Zhi H. et al., "Enzymatic function of hemoglobin as a nitrite reductase that produces NO under allosteric control", The Journal of Clinical Investigation, Vol. 115, pp. 2099-2107 (2005) (NPL 7). However, as will be proved hereinafter in an exemplary experiment 4, sodium nitroprusside (SNP), nitroglycerin (NTG), and other similar general-purpose nitrogen monoxide donor drugs are not recognized to effectively suppress aggravation of retinopathy or have an angiogenesis regulation effect, and accordingly, the effect of the present invention is a significantly specific pharmacological action limited to nitrate and nitrite. In other words, it is believed that the angiogenesis regulation effect by nitrate and nitrite in the present invention is not simply attributed to an increase in quantity supplied of nitrogen monoxide but involves a mechanism found by the present inventors that is regulations of production of in vivo nitrogen monoxide by nitrate and expression of a vascular endothelial growth factor (VEGF) by it.

The present composition preferably regulates angiogenesis by maintaining concentration of nitrate ions in a subject within an effective range. It enables to regulate angiogenesis in ophthalmologic diseases, inflammatory disease and malignant neoplasm, and in particular, it is effective in regulating angiogenesis in at least one ophthalmologic disease selected from retinopathy of prematurity, diabetic retinopathy, age-related macular degeneration and neovascular glaucoma. The present composition as described above can reduce retinal avascular area by suppressing pathologic neovascularization without inhibiting physiological revascularization, and it can suppress intravitreous pathologic neovascularization.

Herein, nitrite salt is rapidly oxidized by hemoglobin and present in blood mostly as nitrate salt (nitrite ions are 5% or less than nitrate ions), and, as described above, both nitrite and nitrate salts are mutually convertible in subject's body via intestine-salivary-gland circulation and so on, and for example, therapeutically effective concentration of present composition can be defined by plasma concentration of nitrate ions. More specifically, the present composition preferably contains an active ingredient in such an amount that the composition provides a plasma concentration of nitrate ions within a range of 8 μmol/L to 1000 μmol/L (suitably, 16 μmol/L to 400 μmol/L, more suitably 32 μmol/L to 200 μmol/L) when it is administered to a subject. When the present composition administered to a subject provides a plasma concentration of nitrate ions of less than 8 μmol/L, it is possible that disease treatment/prevention is not enough because of insufficient angiogenesis regulation. In contrast, when the present composition administered to subject provides a plasma concentration of nitrate ions exceeding 1000 μmol/L, bleeding tendency is rarely increased in retinopathy and so on. In addition, plasma concentration of nitrate ions can be determined by separating from admixture in plasma with high performance liquid chromatography followed by direct spectrophotometric measurement, or by the Griessk method and so on.

The present composition may be prepared as a pharmaceutical preparation, or may be applied as a so-called supplement or something as at least one selected from health food, functional food, food for specified health use and dietary supplement.

Because nitrate and nitrite are soluble in water and satisfactorily absorbable via a digestive tract, the present composition is susceptible of various dosage forms regardless of oral or parenteral administration. The composition can be administered through various routes such as intravenously, endoperitoneally, intramuscularly, subcutaneously, intrapulmonarily, nasally, and externally and locally, and its dosage form includes an injectable form, an inhalable form, and the like. On the other hand, the oral dosage form is exemplified by tablets, capsules, granules, powder, peroral liquid preparations and so on, and nitrate and nitrite are released at desired site in digestive tract by preparing these pharmaceutical preparations for a gastric disintegrating system, an enteric coated system or a controlled release type. These dosage forms can be prepared by common methods for pharmaceutical preparations with attention to incompatibility and with the use of pharmaceutically acceptable excipients. In addition, because biological half-lives of nitrate and nitrite are as short as 3-5 hours, controlled-release form is suitable for bringing out the effect of the present invention.

Although the amount of the present composition administered varies with age, body weight, the degree of progress of the disease, the manner of administration, or the administration route, it is not limited to a particular amount as long as it can exhibit the above pharmacological action and its side effect is within an acceptable range. The specific amount of administration is described below: For example, when 15 mol/kg/day of sodium nitrite is administrated to the model mice of oxygen-induced retinal angiogenesis, maximal plasma concentration of nitrate ions reaches around 100 mol/L, and pathologic neovascularization is suppressed without inhibition of physiological retinal neovascularization.

Furthermore, administration period of the present composition is not limited, but preferably the composition is administrated as soon as pathologic neovascularization occurred because the present composition can regulate angiogenesis without inhibition of physiological neovascularization as described hereinafter in exemplary experiment 3. For example, when an angiogenic disease treated or prevented by the present invention is at least one ophthalmologic disease selected from retinopathy of prematurity, diabetic retinopathy, age-related macular degeneration and neovascular glaucoma, administration of the composition is preferably carried out from when a symptom of pathologic neovascularization accompanying the ophthalmologic disease is observed, until physiological neovascularization is sufficiently progressed and tissue ischemia is alleviated.

Furthermore, it is also effective to use the present composition preventively, and retinopathy of prematurity can be prevented from developing into aggravated symptoms by starting to administer the present medicament during high concentration of oxygen therapy, and diabetic retinopathy can be prevented from developing into aggravated symptoms by starting to administer the present medicament when it is observed that a retinal blood vessel bleeds/has edema.

The present invention also provides a method for regulating angiogenesis by administration of the present composition including an active ingredient which is at least one of nitrate, nitrite, and a compound convertible into nitrate or nitrite after it is absorbed into the subject. The details of the present method are similar to description for the invention above.

In the present method, as has been described for the present composition, it is preferable to regulate angiogenesis by maintaining concentration of nitrate ions in a subject within an effective concentration range, and the range is preferably within 8-1000 μmol/L in plasma of a subject.

Furthermore, it is expected that the present method is effective for treatment of wounds and angiogenetic disease which is in particular at least one ophthalmologic disease selected from retinopathy of prematurity, diabetic retinopathy, age-related macular degeneration and neovascular glaucoma, and in the case of these ophthalmologic diseases, administration is preferably carried out from when a symptom of pathologic neovascularization accompanying the ophthalmologic disease is observed, until physiological neovascularization is sufficiently progressed and tissue ischemia is alleviated.

Hereinafter, the present invention will be described more specifically with reference to exemplary experiments, however it is not limited to these instances.

Exemplary Experiment 1: Evaluation of Effect for Reducing Retinal Avascular Area by Nitrate and Nitrite The effect of sodium nitrate and sodium nitrite for reducing retinal avascular area was evaluated by the model mice of oxygen-induced retinal angiogenesis which were generally used for in vivo pathologic neovascularization model in a retinal angiogenic disease.

Preparation of Test Compound Injection

Sodium nitrate or sodium nitrite as a test compound was dissolved in physiological saline for injection to prepare a test compound injection of 3-15 μmol/L.

Experimental Procedure

C57BL/6J mouse (SLC) was used as an experimental animal. The model mice of oxygen-induced retinal angiogenesis were provided according to Smith et al. (e.g., Lois E. H. Smith et al., "Oxygen-Induced Retinopathy in the Mouse", Invest Ophthalmol Vis Sci., Vol. 35, pp. 101-111 (1994) (NPL 8)). Neonatal mice were bred from the 7th day (P7) to the 12th day (P12) after birth together with a parent mouse in a cage of high levels of oxygen (75±1% of $O_2$) controlled by oxygen control equipment (PRO-OX110, produced by Reming Bio-instruments Co) to provide high levels of oxygen (75±1% of $O_2$). Retinal angiogenesis was induced by breeding under normoxic condition (21% of $O_2$) from the 12th day to the 17th day after birth. Sodium nitrate or sodium nitrite was injected to a cervical region hypodermically once per day in amount of 15 or 75 μmol/kg for ten days from the 7th day (P7) to the 16th day (P16) after birth. In addition, physiological saline as controls was similarly injected hypodermically instead of test compound.

Fifty micro grams per animal of fluorescein-conjugated dextran (FITC-dextran; M.W. $2\times10^6$, produced by SIGMA) were systemically perfused from the left ventricle under deep anesthesia with pentobarbital on the 17th day after birth (P17). After the perfusion, eyes of mouse were removed and fixed in a 4% paraformaldehyde phosphate buffer for 4-12 hours. After the fixation, the cornea and the lens were excised from eye, and the residual hyaloid artery was removed by micro tweezers. The retina was separated under a microscope, and subsequently set flat and embedded in VECTASHIELD (produced by Vector Laboratories Inc.) for preparation of a retinal flat-mount.

Method of Evaluation of Retinal Avascular Area

Flat mounted retinas were imaged with a high sensitivity CCD camera under a fluorescent inverted microscope (Olympus IX71). A value of total retinal area and a value of retinal avascular area in obtained image were converted to numeric data by Photoshop CS4 extended (Adobe), and a value of areal ratio of retinal avascular area in comparison with the value of total retinal area was calculated by the following equation:

value of areal ratio of retinal avascular area=value of retinal avascular area (μm$^2$)/value of total retinal area (μm$^2$)×100

Result and Effect

FIG. 1 showed a fluorescence imaging of retinal vessel obtained as a result of an exemplary experiment 1, and FIGS. 1(a), 1(b), 1(c) and 1(d) were indicated in the case of administration of 15 μmol/kg of sodium nitrite, 75 μmol/kg of sodium nitrite, 75 μmol/kg of sodium nitrate, and physiological saline, respectively. Also the average of values of retinal avascular area, the average of values of total retinal area and the average of values of calculated areal ratio of retinal avascular area were shown in Table 1.

TABLE 1

|  | value of retinal avascular area ($\mu m^2$) | value of total retinal area ($\mu m^2$) | value of areal ratio of retinal avascular area |
| --- | --- | --- | --- |
| 15 µmol/kg of sodium nitrite | 417863.94 | 6483871.44 | 6.44% |
| 75 µmol/kg of sodium nitrite | 571705.28 | 5711629.25 | 10.01% |
| 75 µmol/kg of sodium nitrate | 842271.02 | 6629478.87 | 12.7% |
| physiological saline | 1058286.827 | 6502029.511 | 16.28% |

In the retinal angiogenic disease model, retinal avascular area was reduced by approximately 20% and approximately 40-60% as compared to control group by administration of nitrate and nitrite, respectively. These results have revealed that nitrate and nitrite regulate pathologic neovascularization without inhibiting physiological retinal neovascularization and have an effect to reduce retinal avascular area.

Exemplary Experiment 2: Evaluation of Suppression Effect of Pathologic Neovascularization The effect of sodium nitrate and sodium nitrite for suppression of pathologic neovascularization by oxygen-induced retinal vascularized model was evaluated.

Preparation of Test Compound Injection

Sodium nitrate or sodium nitrite as a test compound was dissolved in physiological saline for injection to prepare a test compound injection of 3-15 µmol/L.

Experimental Procedure

C57BL/6J mouse (SLC) was used as an experimental animal. The model mice of oxygen-induced retinal angiogenesis were prepared according to exemplary experiment 1. Sodium nitrate or sodium nitrite was injected to a cervical region hypodermically once per day in amount of 15 or 75 µmol/kg for ten days from the 7th day (P7) to the 16th day (P16) after birth. In addition, physiological saline as controls was similarly injected hypodermically instead of test compound.

On the 17th day after birth (P17), the mice were euthanised by overdose of pentobarbital, and eyes were removed together with optic nerve. The eyes were washed in physiological saline, excessive tissues were excised, and the eyes were thus fixed in a 4% paraformaldehyde phosphate buffer for 12 hours. After the fixation, the eyes were dehydrated by immersing in a graded ethanol series of 70-100% sequentially and were embedded in paraffin. The obtained paraffin blocks were sliced parallel to the optic nerve with 4-µm thickness at 50-µm intervals and stained with hematoxylin eosin (HE-stain), and subsequently, retinal sectioning specimens were observed with an inverted microscope (Olympus IX71) to count the number of pathological vessels breaking the inner limiting membrane and extending into the vitreum.

Result and Effect

Figure 2:
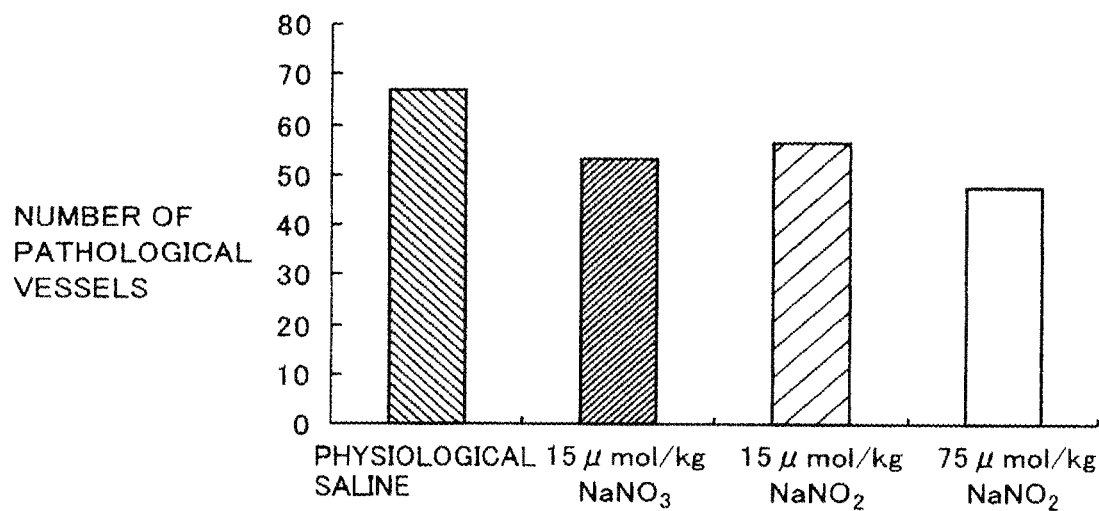
FIG. 2 is a graph which shows the comparison of the number of pathological vessels entered into the vitreous body in the case of administration of physiological saline, 15 μmol/kg of sodium nitrate, 15 μmol/kg of sodium nitrite and 75 μmol/kg of sodium nitrite, with the ordinate showing the number of pathological vessels.
Figure 3:
FIG. 3 shows an image of retina in cross section when physiological saline is administered as a control.

FIG. 2 is a graph which showed the comparison of the number of pathological vessels entered into the vitreous body in the case of administration of physiological saline, 15 µmol/kg of sodium nitrate, 15 µmol/kg of sodium nitrite and 75 µmol/kg of sodium nitrite, with the ordinate showing the number of pathological vessels. FIG. 3 showed an image of retina in cross section when physiological saline was administered as a control. At the part indicated by an arrow, it was found that pathological vessel broke the inner limiting membrane and extended to the vitreum. From graph in FIG. 2, the number of pathological vessels breaking the inner limiting membrane and extending into the vitreum was decreased by administration of sodium nitrate or sodium nitrite. Furthermore, the number of pathological vessels tended to decrease with increase in amount of nitrite administration, and it was observed that pathological vessels reduced by approximately 30% as compared with a control in the group with 75 µmol/kg of nitrite administered. These results have revealed that nitrate and nitrite have an effect to suppress pathologic neovascularization in the vitreum without inhibiting physiological neovascularization.

Exemplary Experiment 3: Evaluating Effect of Nitrate and Nitrite in Regulating Retinal Angiogenesis For the model mice of oxygen-induced retinal angiogenesis, retinal angiogenesis is induced by providing 75% oxygen followed by breeding in room air during P12-P17. Therefore the effect of angiogenesis regulation of the invention was clearly examined by administration of sodium nitrate or sodium nitrite from the beginning of retinal angiogenesis (or from P12).

Preparation of Test Compound Injection

Sodium nitrate or sodium nitrite as a test compound was dissolved in physiological saline for injection to prepare a test compound injection of 3 µmol/L.

Experimental Procedure

Preparation of the model mice of oxygen-induced retinal angiogenesis, fluorescent imaging of retinal vessels and a retinal flat-mount were operated according to exemplary experiment 1. However sodium nitrate or sodium nitrite was injected to a cervical region hypodermically once per day in amount of 15 µmol/kg for ten days from the 12th day (P12) to the 16th day (P16) after birth. In addition, physiological saline as controls was similarly injected hypodermically instead of test compound for the same period of time.

Method of Evaluation of Retinal Avascular Area

Areal ratio of retinal avascular area was calculated pursuant to exemplary experiment 1.

Result and Effect

Figure 4:
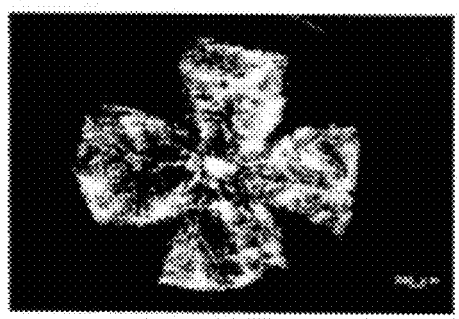
FIG. 4 shows a fluorescence imaging of retinal vessel obtained as a result of an exemplary experiment 3.
Figure 4:
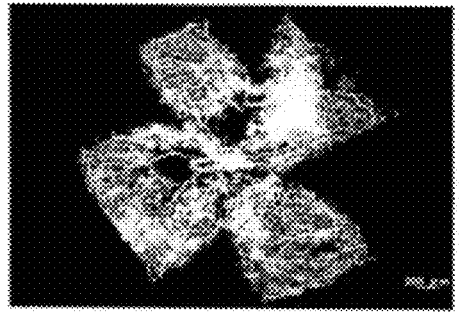
Figure 4:
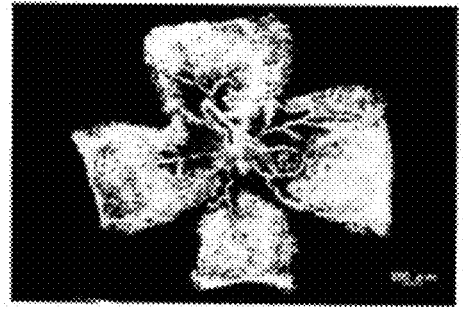

FIG. 4 showed a fluorescence imaging of retinal vessel obtained as a result of an exemplary experiment 3, and FIGS. 4(a), 4(b), and 4(c) were indicated in the case of administration of 15 µmol/kg of sodium nitrate, 15 µmol/kg of sodium nitrite, and physiological saline, respectively. Also the average of values of retinal avascular area, the average of values of total retinal area and the average of values of calculated areal ratio of retinal avascular area were shown in Table 2.

TABLE 2

|  | value of retinal avascular area ($\mu m^2$) | value of total retinal area ($\mu m^2$) | value of areal ratio of retinal avascular area |
| --- | --- | --- | --- |
| 15 µmol/kg of sodium nitrate | 506451.72 | 5782966.84 | 8.76% |
| 15 µmol/kg of sodium nitrite | 621218.70 | 6688088.68 | 9.3% |
| physiological saline | 1060520.67 | 6629788.95 | 16.0% |

When sodium nitrate or sodium nitrite was administered from the start of retinal angiogenesis, an approximately 40% reduction of retinal avascular area was observed in comparison with a control group. This result has revealed that nitrate and nitrite regulate an angiogenesis process and suppress pathologic neovascularization without inhibiting physiological neovascularization and have an effect to reduce retinal avascular area.

Exemplary Experiment 4: Comparing Effect of Nitrite with that of General-Purpose Nitrogen Monoxide Donor Drug in Reducing Retinal Avascular Area Using the model mice of oxygen-induced retinal angiogenesis, presence/absence of an effect to reduce retinal avascular area was examined for a nitrogen monoxide donor drug generally used for angina pectoris, as an antihypertensive, and so on, to clarify that the present invention has an effect with specificity.

Preparation of Test Compound Injection and Injection for Comparative Example

Sodium nitrite as a test compound was dissolved in physiological saline for injection to prepare a test compound injection of 3 μmol/L. As comparative examples, sodium nitroprusside (SNP), which was a nonenzymatic nitrogen monoxide donor drug, and nitroglycerin (NTG), which was an enzymatic nitrogen monoxide donor drug, were selected. SNP dehydrate as a comparative example was dissolved in physiological saline for injection to prepare a comparative example injection of 0.4 μmol/L. Furthermore, for NTG, 50 mg of nitroglycerin injection "HK" (HIKARI PHARMACEUTICAL) was intactly used as an injection for a comparative example.

Experimental Procedure

Preparation of the model mice of oxygen-induced retinal angiogenesis, fluorescent imaging of retinal vessels and a retinal flat-mount were operated according to exemplary experiment 1. Sodium nitrite, SNP and NTG were injected to a cervical region hypodermically once per day in amounts of 15 μmol/kg, 2 μmol/kg, and 20 μmol/kg, respectively, for ten days from the 7th day (P7) to the 16th day (P16) after birth.

Method of Evaluation of Retinal Avascular Area

Areal ratio of retinal avascular area was calculated pursuant to exemplary experiment 1.

Result and Effect

Figure 5:
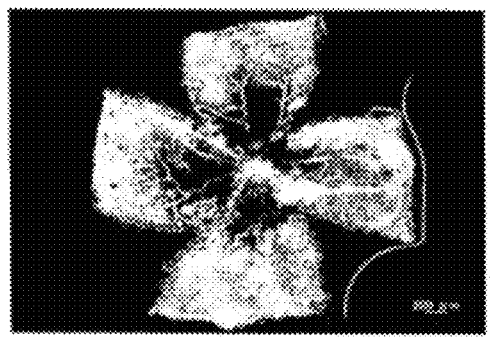
FIG. 5 shows a fluorescence imaging of retinal vessel obtained as a result of an exemplary experiment 4.
Figure 5:
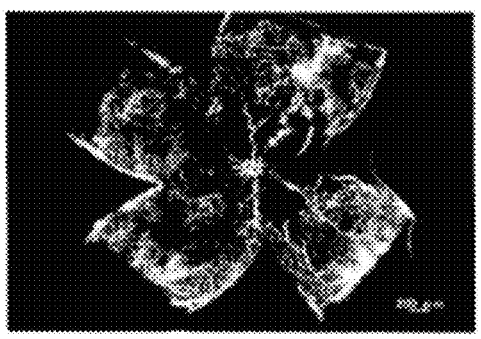
Figure 5:
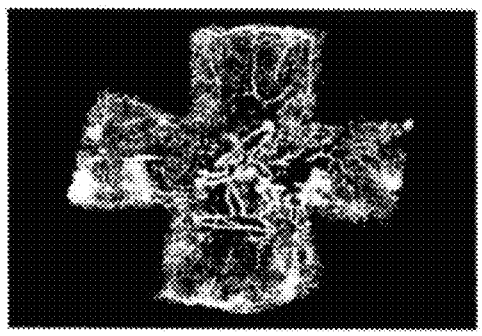

FIG. 5 showed a fluorescence imaging of retinal vessel obtained as a result of an exemplary experiment 4, and FIGS. 5(a), 5(b), and 5(c) were indicated in the case of administration of sodium nitroprusside (SNP), nitroglycerin (NTG), and 15 μmol/kg of sodium nitrite, respectively. Also the average of values of retinal avascular area, the average of values of total retinal area and the average of values of calculated areal ratio of retinal avascular area were shown in Table 3.

TABLE 3

| | value of retinal avascular area ($\mu m^2$) | value of total retinal area ($\mu m^2$) | value of areal ratio of retinal avascular area |
|---|---|---|---|
| SNP administered | 1076584.43 | 6443554.78 | 16.7% |
| NTG administered | 1456421.33 | 6817842.90 | 21.36% |
| 15 μmol/kg of sodium nitrite | 417863.94 | 6483871.44 | 6.44% |

In a pathologic neovascularization model in a retinal angiogenic disease, it was observed that retinal avascular area was increased by approximately 2.5 times and approximately 3.3 times with respect to SNP and NTG, respectively, in comparison with a group administered with nitrite. Neither SNP nor NTG was observed to reduce a typical symptom of retinopathy, or avascular area, and it has been clarified that the effect of the present invention is specific to nitrate and nitrite.

Exemplary Experiment 5: Comparing Nitrite as Therapeutic Agent for Retinopathy with VEGF Inhibitor Using the model mice of oxygen-induced retinal angiogenesis, a comparison was made about retinopathy treatment effect between nitrite and an anti-VEGF antibody used for treatment of progressive colorectal cancer, age-related macular degeneration and so on.

Preparation of Test Compound Injection and Injection for Comparative Example

Sodium nitrite as a test compound was dissolved in physiological saline for injection to prepare a test compound injection of 3 μmol/ml. For a comparative example, a murine monoclonal anti-VEGF antibody (produced by SANTACRUZ BIOTECHNOLOGY, INC.) was condensed to prepare 500 μg IgG/ml of an injection for the comparative example.

Experimental Procedure

Preparation of the model mice of oxygen-induced retinal angiogenesis, fluorescent imaging of retinal vessels and a retinal flat-mount were operated according to exemplary experiment 1. Sodium nitrite was injected to a cervical region hypodermically once per day in amount of 15 μmol/kg for ten days from the 7th day (P7) to the 16th day (P16) after birth. The anti-VEGF antibody was injected through the corneal limbus to the vitreous body with a microsyringe equipped with a 33G hypodermic needle, by cutting mice eyelids open when oxygenation ended (on the 12th day after birth).

Method of Evaluation of Retinal Avascular Area

Areal ratio of retinal avascular area was calculated pursuant to exemplary experiment 1.

Result and Effect

Figure 6:
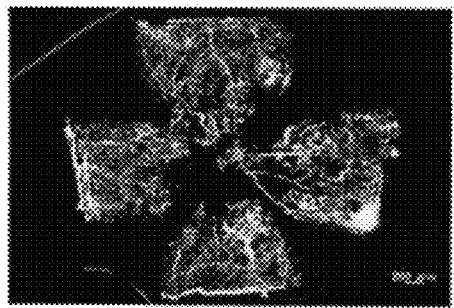
FIG. 6 shows a fluorescence imaging of retinal vessel obtained as a result of an exemplary experiment 5.
Figure 6:
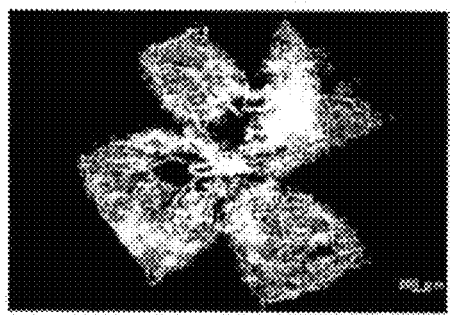

FIG. 6 showed a fluorescence imaging of retinal vessel obtained as a result of an exemplary experiment 5, and FIGS. 6(a) and 6(b) were indicated in the case of administration of anti-VEGF antibody, and 15 μmol/kg of sodium nitrite, respectively. Also the average of values of retinal avascular area, the average of values of total retinal area and the average of values of calculated areal ratio of retinal avascular area were shown in Table 4.

TABLE 4

| | value of retinal avascular area ($\mu m^2$) | value of total retinal area ($\mu m^2$) | value of areal ratio of retinal avascular area |
|---|---|---|---|
| anti-VEGF antibody | 1186758.21 | 6357103.66 | 18.7% |
| 15 μmol/kg of sodium nitrite | 621218.70 | 6688088.68 | 9.3% |

When the retinopathy treatment effect of nitrite and that of the anti-VEGF antibody were evaluated in terms of reduction of retinal avascular area, the proportion of the retinal avascular area of a group having the anti-VEGF antibody administered was 18.7%, whereas the proportion of the retinal avascular area of a group having nitrite administered was 9.3%, and significant reduction of retinal avascular area was observed. This result suggested that the anti-VEGF antibody's action to inhibit angiogenesis did not have selectivity and inhibited not only pathologic neovascularization but also physiological neovascularization. In contrast, nitrite suppresses pathologic neovascularization without inhibiting physiological neovascularization, and thus effectively reduces retinal avascular area. While the present invention has only a limited systemic side effect as compared with an anti-VEGF antibody, as described above, it has also been revealed that the present invention is also superior in treating without leaving avascular area in retina.

Exemplary Experiment 6: Estimating Optimal Plasma Concentration of Nitrate Ions Causing Angiogenesis Regulation Effect Using the model mice of oxygen-induced retinal angiogenesis, an optimal plasma concentration of nitrate ions was estimated in the case where a significant therapeutic/preventive effect was observed for an ophthalmologic angiogenic disease by administration of the present composition.

Preparation of Test Compound Injection

Sodium nitrate or sodium nitrite as a test compound was dissolved in physiological saline for injection to prepare a test compound injection of 3-15 μmol/L.

Experimental Procedure

C57BL/6J mouse (SLC) was used as an experimental animal. The model mice of oxygen-induced retinal angiogenesis were prepared according to exemplary experiment 1. Sodium nitrate or sodium nitrite was injected by single dose administration in amounts of 15, 75 and 150 μmol/kg, which were dosages observed as having a significant therapeutic/preventive effect in the present invention, to a cervical region hypodermically on the 12th day (P12) after birth when 75% oxygenation ended. Thereafter, isoflurane was used to anesthetize the mice, and 150 μl of blood was collected from the abdominal aorta over time. Plasma concentration of nitrate ions was measured by ion exchange chromatography using a normal phase column under the following conditions:

Conditions for Ion Exchange Chromatography

Separation column: Asahipak NH2P-50 4E (4.6 mm×250 mm)

Guard column: Inertsil NH2 (5 μm) (4 mm×10 mm)

Mobile phase: 10 mM of sodium dihydrogenphosphate, 150 mM of sodium perchlorate, 5.0

Flow rate: 0.7 ml/min

Detection wavelength: 210 nm

Result and Effect

Figure 7:
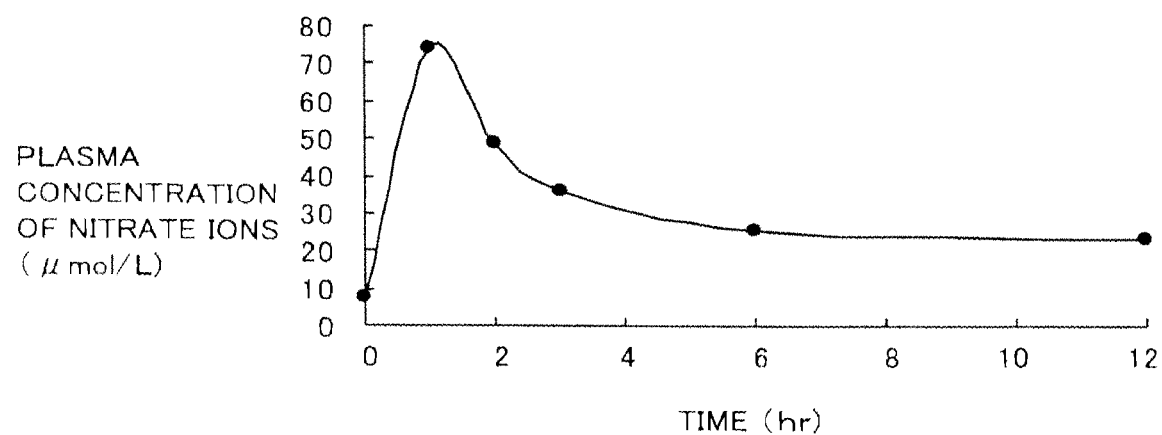
FIG. 7 shows transition of plasma concentration of nitrate ions with time when 15 μmol/kg of sodium nitrite is administered to a mouse subcutaneously in a cervical region, as obtained as a result of an exemplary experiment 6.

FIG. 7 showed transition of plasma concentration of nitrate ions with time when 15 μmol/kg of sodium nitrite was administered to a mouse subcutaneously in a cervical region, as obtained as a result of exemplary experiment 6. Furthermore, when sodium nitrate was administered in amounts of 15 μmol/kg, 75 μmol/kg, and 150 μmol/kg in a cervical region subcutaneously, it provided maximum plasma concentration of nitrate ions for each amount, averaged as shown in Table 5.

TABLE 5

| | maximum plasma concentration of nitrate ions after single-dose administration (μmol/L) |
|---|---|
| 15 μmol/kg of sodium nitrate | 135.38 |
| 75 μmol/kg of sodium nitrate | 194.9 |
| 150 μmol/kg of sodium nitrate | 390.26 |

As is apparent from FIG. 7, it can be seen that nitrite was absorbed within 1 hour after administration, and most thereof was rapidly oxidized by hemoglobin to nitrate, and systemically circulated. That is, in the present invention, it is also clear that when the present composition containing nitrite is administered to a subject, the present invention's therapeutic/preventive effect can be monitored by measuring and managing plasma concentration of nitrate ions, rather than measuring a significantly low plasma concentration of nitrite ions. The table 5 result has revealed that a maximum plasma concentration of nitrate ions by which the present invention's therapeutic/preventive effect is achieved was provided when 150 μmol/kg of sodium nitrate was administered, and that it had a value of approximately 400 μmol/L.

It should be understood that the embodiments and examples disclosed herein are illustrative and non-restrictive in any respect. The scope of the present invention is defined by the terms of the claims, rather than the description above, and is intended to include any modifications within the scope and meaning equivalent to the terms of the claims.

The invention claimed is:

1. A method for treating an ophthalmologic disease in a subject, comprising administering to the subject in need thereof a composition containing as an active ingredient at least one of an inorganic nitrate and a compound convertible into inorganic nitrate after said compound is absorbed into the subject, wherein the composition reduces retinal avascular area and suppresses intravitreous pathologic neovascularization.

2. The method according to claim 1, wherein the composition suppresses pathologic neovascularization by maintaining a nitrate ion concentration in an effective concentration range in the subject.

3. The method according to claim 1, further comprising providing a plasma concentration of nitrate ions in the subject within a range of 8 μmol/L 1000 μmol/L.

4. The method according to claim 1, further comprising providing a plasma concentration of nitrate ions in the subject within a range of 32 μmol/L to 200 μmol/L.

5. The method according to claim 1, wherein the angiogenic, ophthalmologic disease is at least one disease selected from the group consisting of retinopathy of prematurity, diabetic retinopathy, age-related macular degeneration, and neovascular glaucoma.

* * * * *